(12) United States Patent
Kwirandt

(10) Patent No.: US 8,324,559 B2
(45) Date of Patent: Dec. 4, 2012

(54) BOTTLE INSPECTION APPARATUS WITH IMAGE-CORRECTED MIRROR CABINET

(75) Inventor: Rainer Kwirandt, Barbing (DE)

(73) Assignee: Krones AG, Neutraubling (DE)

( * ) Notice: Subject to any disclaimer, the term of this patent is extended or adjusted under 35 U.S.C. 154(b) by 490 days.

(21) Appl. No.: 12/641,445

(22) Filed: Dec. 18, 2009

(65) Prior Publication Data
US 2010/0155580 A1    Jun. 24, 2010

(30) Foreign Application Priority Data
Dec. 24, 2008  (DE) .......................... 10 2008 063 076

(51) Int. Cl.
 *G01N 21/90* (2006.01)
(52) U.S. Cl. ............... 250/223 B; 356/239.1; 356/239.5
(58) Field of Classification Search ............... 250/223 B; 356/239.1, 239.2, 239.5, 239.7
See application file for complete search history.

(56) References Cited

U.S. PATENT DOCUMENTS

| 4,509,081 | A |   | 4/1985  | Peyton et al. |
| 5,256,871 | A |   | 10/1993 | Baldwin |
| 6,072,575 | A | * | 6/2000  | Loll .......................... 356/239.4 |

FOREIGN PATENT DOCUMENTS

| DE | 19534347 A1 | 4/1996 |
| DE | 29919761 U1 | 12/2000 |
| EP | 0663069 A1 | 7/1995 |
| EP | 1985997 A1 | 10/2008 |

\* cited by examiner

*Primary Examiner* — Tony Ko
(74) *Attorney, Agent, or Firm* — Marshall, Gerstein & Borun LLP

(57) ABSTRACT

An inspection apparatus for optically examining bottles, having a mirror cabinet for imaging different circumferential side views of a bottle to be examined. The deflection mirrors for beam paths associated with lateral image areas are tilted such that an image distortion caused by central projection will be compensated for in the lateral image areas.

14 Claims, 3 Drawing Sheets

BOTTLE INSPECTION APPARATUS WITH IMAGE-CORRECTED MIRROR CABINET

CROSS-REFERENCE TO RELATED APPLICATION

The present application claims the benefit of priority of German Patent Application No. 102008063076.4, filed Dec. 24, 2008. The entire text of the priority application is incorporated herein by reference in its entirety.

FIELD OF THE DISCLOSURE

The disclosure relates to an inspection apparatus for optically examining bottles and containers, respectively, and having: an image recording device for producing an image with a plurality of horizontally juxtaposed image areas, at least two of these image areas being arranged laterally of the middle of the image; and a mirror cabinet comprising a plurality of beam paths for deflecting, in the direction of the image areas, different circumferential side views of a bottle to be examined, each beam path having provided therein separate deflection mirrors whose respective elevation with respect to a base plate is defined.

BACKGROUND

Inspection apparatuses for bottles are used e.g. in beverage bottling lines for detecting damaged or dirty bottles. As is generally, known different circumferential views of the bottle side wall are produced simultaneously in a mirror cabinet and imaged onto juxtaposed areas of an imaging sensor. Such apparatuses are disclosed e.g. in EP 0663069 or in DE 19534347.

It is generally desired to image all the views with the least possible amount of distortion, in identical size and without stray light reflections on the bottle surface in transmitted light.

In order to be able to examine the bottle side wall down to the bottom dome in transmitted light, the position from which the bottle is viewed must, however, be only slightly above the bottom of the bottle. It follows that the perspective in the direction of the bottle will be directed at an oblique angle upwards and, in the case of the demanded focal lengths of the objective lens, this will cause the undesired distorted line effect. The larger the distance between the respective object edge and the middle of the image is, the more disturbing this will be. When a plurality of bottle views is projected onto an image area in juxtaposition, the upper areas of the imaged bottles, especially those in the vicinity of the lateral edge of the image, seem to tilt towards the middle.

From DE 19534347 it is known to arrange deflection mirrors on three-point kinematic mounts and to translate and/or rotate the position of the individual bottle views on the image plane by rotating these mirrors about a horizontal and a vertical axis. Distorted lines can, however, not be corrected in this way.

SUMMARY OF THE DISCLOSURE

It is an aspect of the present disclosure to avoid the above-described drawbacks.

Two of the separate deflection mirrors for beam paths associated with the lateral image areas are tilted relative to a normal to the base plate in such a way that an image distortion caused by central projection will be compensated for in the lateral image areas. Distorted lines can therefore be compensated for each beam path separately, so that all the imaged bottles will be substantially upright in the image.

A preferred embodiment is so conceived that, in the beam paths associated with the lateral image areas, the elevation of one of the separate deflection mirrors is fixed and the elevation of the other separate deflection mirror is adjustable. The number of components to be adjusted is reduced in this way.

A preferred embodiment is so conceived that, in the beam paths associated with the lateral image areas, one separate deflection mirror is inclined at an oblique angle upwards and another deflection mirror is inclined at an oblique angle downwards. Image distortion is eliminated in a particularly effective manner in this way.

A preferred embodiment is so conceived that, in the beam paths associated with the lateral image areas, the absolute values of the tilting angles of the separate deflection mirrors relative to the normal to the base plate range from $0.01°$ to $1°$. This allows a flexible arrangement of the components in the mirror cabinet. In addition, commercially available components can be used for adjusting the elevation.

According to a preferred embodiment, the separate deflection mirrors for beam paths associated with the lateral image areas are tilted in such a way that the projected side views in the image are additionally oriented vertically to one another. The number of mounting steps can be reduced in this way.

According to a preferred embodiment, the separate deflection mirrors are, with a fixed elevation, secured in position on holders having a mounting surface that is inclined in accordance with the elevation of these deflection mirrors. This allows a precise, stable and reproducible inclination of the deflection mirrors.

According to a preferred embodiment, the separate deflection mirrors for the beam path associated with the central image area are arranged at right angles to the base plate. The beam path can thus be realized at low cost and with a minimum amount of adjustment effort.

According to a preferred embodiment, each beam path has provided therein two separate deflection mirrors. This allows beam deflection with a minimum number of optical components. In addition, the direction of rotation of circularly polarized light changes, due to reflection, equally frequently in all beam paths.

According to a preferred embodiment, the base plate is oriented substantially at right angles to the symmetry axis of the bottle. The mirror cabinet can be mounted and adjusted more easily in this way.

In the known apparatuses, the beam paths for all bottle views are, for the sake of producing a sharp image, dimensioned such that they have substantially identical lengths between the bottle and the image plane, as has been described e.g. in EP 0663069. This, however, produces the undesirable effect that the bottle views in the image appear to be increasingly large the further they are imaged from the middle of the image.

It is a further aspect of the present disclosure to avoid this drawback.

According to these embodiments, the beam paths associated with the lateral image areas are longer than the beam path associated with the central image area, the lengths of the beam paths being graded such that the side views of the bottle in the image areas have substantially the same size. The image quality and the evaluation of the bottle views can be improved in this way. This measure, on its own, offers the aimed-at advantages.

Alternatively, the length of the beam paths associated with the lateral image areas increases as the distance between the image area associated with the respective beam path and the middle of the image increases, the lengths of the beam paths being graded such that the side views of the bottle in the image areas have substantially the same size. Also this measure offers, on its own, the aimed-at advantages.

According to a preferred embodiment, the length ratio of beam paths associated with juxtaposed image areas lies between 1.005 and 1.02. It is thus possible to adapt the bottle size for different beam paths and to produce also a sharp image.

According to a preferred embodiment, the inspection apparatus additionally comprises a light source for exposing the bottle to transmitted light. This allows the generation of particularly contrasty images.

According to a preferred embodiment, a shade is provided between the beam paths, said shade preventing light emitted by the light source to be redirected onto the bottle due to multiple reflection on at least two of the deflection mirrors. Stray light reflections which cannot be avoided by optimizing the mirror array alone can be suppressed in the mirror cabinet in this way.

BRIEF DESCRIPTION OF THE DRAWINGS

One embodiment of the present disclosure is shown hereinbelow in the drawing, in which.

DETAILED DESCRIPTION OF THE PREFERRED EMBODIMENT

Figure 1:
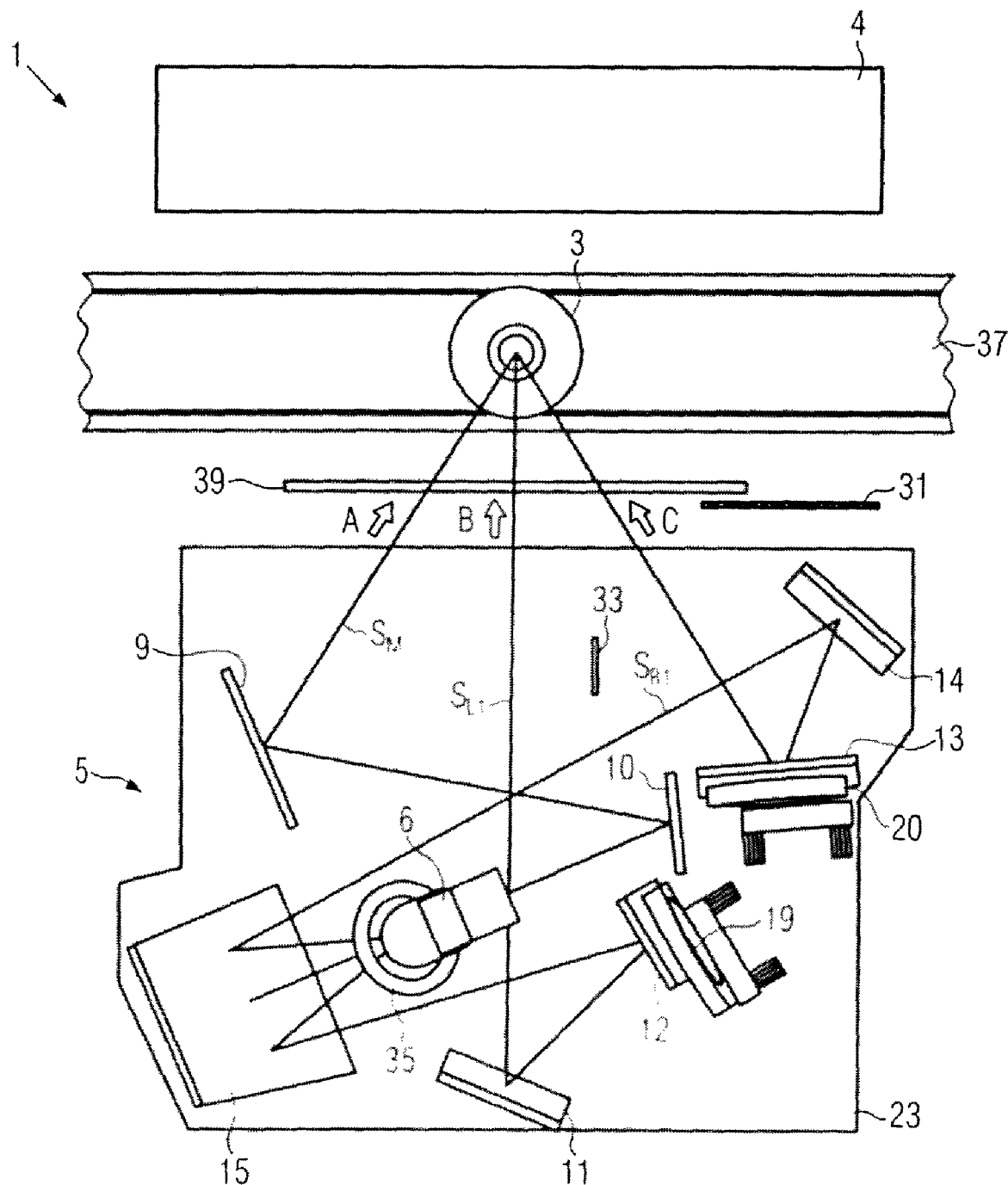
FIG. 1 shows a perspective top view of an inspection apparatus according to the present disclosure.
Figure 2:
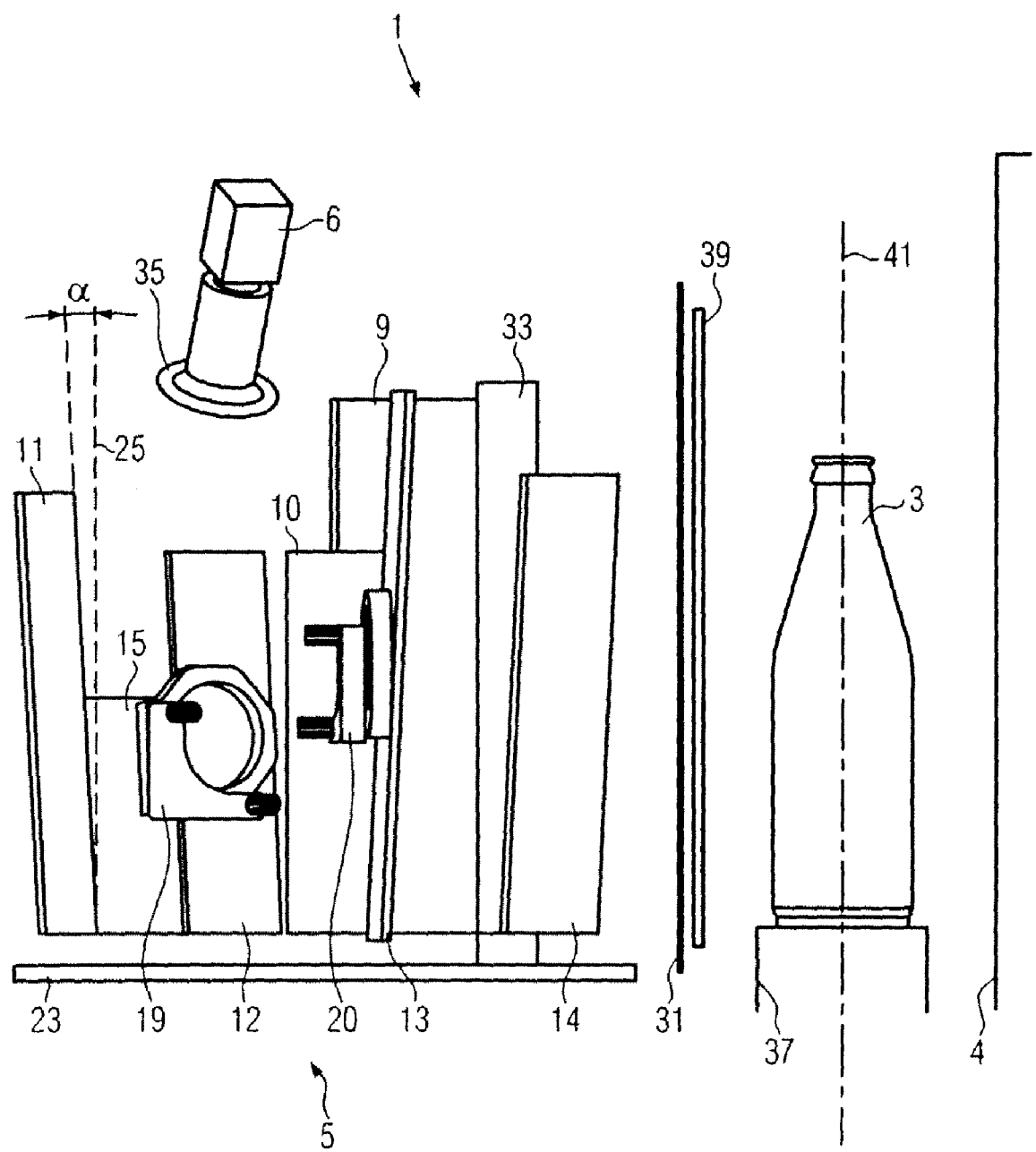
FIG. 2 shows a perspective side view of the array according to FIG. 2.

According to FIGS. 1 and 2, an inspection apparatus 1 according to the present disclosure comprises a light source 4 for examining transparent bottles 3 in transmitted light, e.g. circularly polarized light, and a mirror cabinet 5 with three beam paths $S_M$, $S_{L1}$, $S_{R1}$ for imaging three bottle views A, B, C by means of an image recording device 6, such as a semi-conductor camera, said bottle views A, B, C being circumferentially rotated with respect to one another by preferably 30° or approximately 45°.

Figure 3:
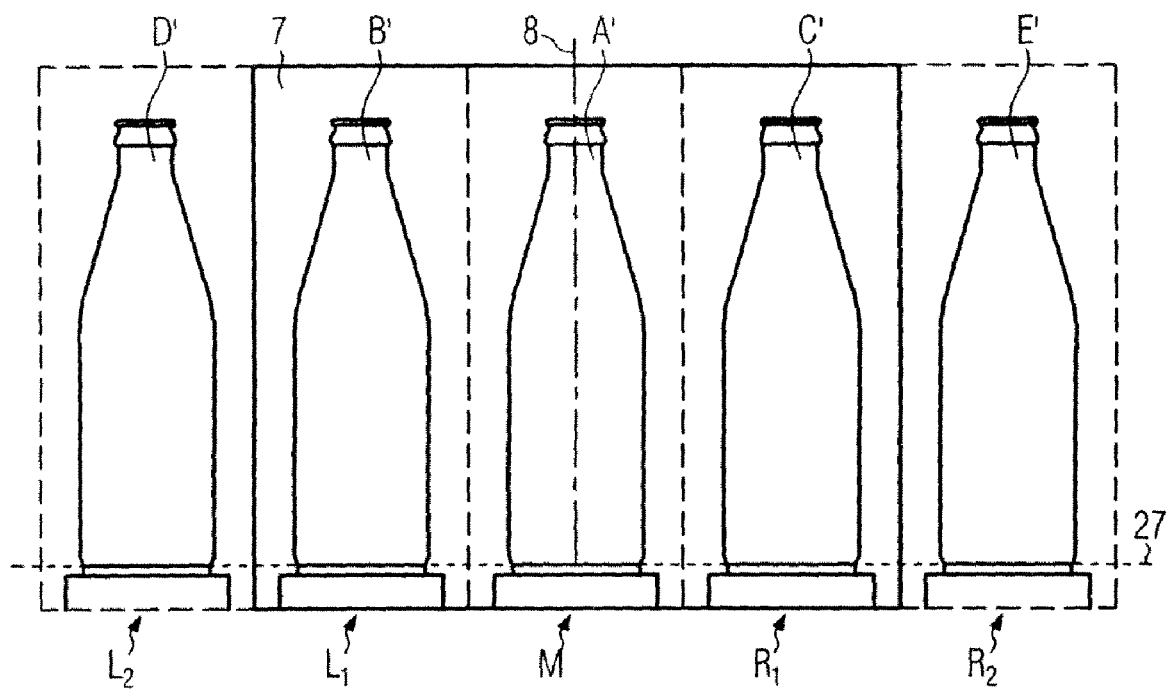
FIG. 3 shows a schematic representation of an image with different views of a bottle to be examined on juxtaposed image areas.

FIG. 3 shows an image 7 produced by the image recording device 6 e.g. on a screen (not shown), said image 7 being horizontally divided into image areas, viz. a central area M, a left lateral area $L_1$ and a right lateral area $R_1$, in which the projected bottle views A', B' and C' are imaged.

Starting from the bottle 3, the deflection mirrors 9 and 10 deflect the beam path SM via the deflection mirror 15, which is common to all the beam paths $S_M$, $S_{L1}$, $S_{R1}$, into the central image area M, the deflection mirrors 11 and 12 deflect the beam path $S_{L1}$ into the left lateral image area $L_1$, and the deflection mirrors 13 and 14 deflect the beam path $S_{R1}$ into the right lateral image area $R_1$ of the image recording device 6. In FIG. 1 only the respective beam axis of the beam paths $S_M$, $S_{L1}$, $S_{R1}$ is shown.

The deflection mirrors 9, 10, 11 and 14 are secured in position on a common base plate 23 by means of fixed holders 16, 17, 18 and 21, which, for the sake of clarity, are not shown in FIGS. 1 and 2; the deflection mirrors 12 and 13 are fixed to said base plate 23 by means of adjustable holders 19 and 20.

For the sake of clarity, only the optical components are shown in FIGS. 1 and 2, whereas the associated mounting elements for fixing the components to the base plate 23 are not shown, such mounting elements being e.g. bases for the adjustable holders 19 and 20 as well as holders for the common deflection mirror 15 or the image recording device 6.

The mirrors 9 and 10 are arranged such that they extend at right angles to the base plate 23. The mirror 11 is inclined at an angle α relative to a normal 25 to the base plate 23, the mirror 12 at an angle β, the mirror 13 at an angle γ and the mirror 14 at an angle δ. FIG. 2 shows, for the sake of clarity, only the angle α. In FIGS. 1 and 2, the elevations of the mirrors 9 to 14 are shown exaggeratedly so as to make the figures more easily understandable.

Figure 4:
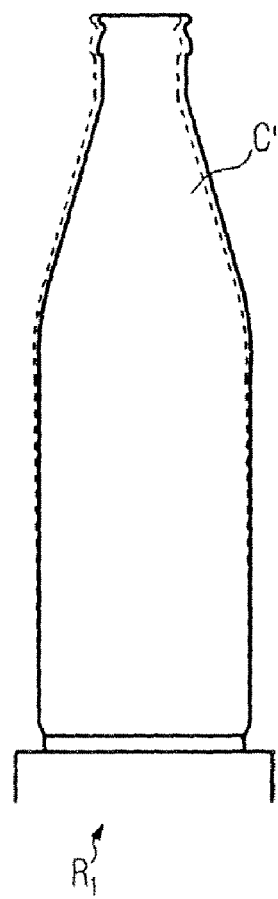
FIG. 4 shows a schematic representation of an imaged bottle view after an image distortion caused by distorted lines has been corrected according to the present disclosure.

The angles α-δ are dimensioned such that the bottle views A', B' C' shown in the image areas M, $L_1$ and $R_1$ seem to be positioned on a common horizontal base line 27 in the image and that, simultaneously, the distorted line effect caused by central projection is minimized in the lateral image areas $L_1$ and $R_1$. This effect is schematically indicated in FIG. 4 by the broken line. In lateral image areas, vertical lines are therefore inclined inwards, especially in the upper half of the image. This perspective distortion is largely compensated for by the combined effect of the tilting angles α and β as well as γ and δ, so that vertical edges or boundaries of objects are imaged largely vertically in image 7, as indicated in FIG. 4 by the view C' depicted by a solid line.

The length $I_M$ of the beam path $S_M$ directed towards the central image area M is smaller than the lengths $I_{L1}$ and $I_{R1}$ of the beam paths $S_{L1}$ and $S_{R1}$, which are directed towards the lateral image areas $L_1$ and $R_1$ and which are identical in length, so that the bottle views A', B' and C' imaged in the image areas M, L and R appear to be of identical size in image 7.

Making use of such adapted lengths $I_M$, $I_{L1}$ and $I_{R1}$, a situation is simulated in the case of which three identically sized, juxtaposed bottles 3 would be projected in identical size onto the image areas $L_1$, M and $R_1$ by the image recording device 6 without using a mirror cabinet 5. This would be the case if the bottles 3 were positioned in an object plane that extends parallel to the image plane. If, in this arrangement, e.g. the bottle 3 positioned centrally in front of the image recording device and the bottle 3 on the right hand side were viewed, these bottles would define a right-angled triangle with the image recording device 6. Seen from the image recording device 6, the lengths of the associated beam paths between the image recording device 6 and the bottles 3 would then behave like the adjacent leg and the hypotenuse in the triangle defined. The central beam path would therefore be the shorter one.

The inspection apparatus 1 additionally comprises a shield 31 and a shade 33 for reducing stray reflections as well as a polarizing filter 35. For the sake of completeness, a conveyor belt 37 for the bottles 3 and a protective pane 39 are shown.

The light source 4 emits circularly polarized light. The apparatus is, however, not limited to the use of circularly polarized light.

The image recording device 6 is e.g. a conventional semi-conductor camera comprising an objective lens and an iris. The format of the image 7 produced may deviate from the example shown. Especially panorama formats are imaginable, which allow a juxtaposition of more than three views A', B', C' of the bottle. This is indicated in FIG. 3 by the additional lateral image areas $L_2$ and $R_2$ depicted by broken lines. Also an arbitrary even number of image areas is imaginable. When an even number of image areas is provided, a central image area M does not exist. When e.g. four image areas are provided, the image 7 is instead divided into two lateral left image areas $L_1$, $L_2$ and into two lateral right image areas $R_1$, $R_2$. The areas $L_1$ and $R_1$ would in this case adjoin one another in the middle of the image.

The image recording device 6 is supported in a mount, which is not shown, such that it is adapted to be rotated and to be tilted in two planes, e.g. by commercially available, three-point-support mounting elements.

The course of the beam paths $S_M$, $S_{L1}$ and $S_{R1}$ in the mirror cabinet 5 is determined by conventional ray tracing methods. General demands that have to be complied with in this respect are an array which should be as compact as possible and which should comprise the least possible number of optical components. In addition, the number of the separate deflection mirrors 9-14 should be identical for all beam paths $S_M$, $S_{L1}$ and $S_{R1}$ so as to obtain comparable bottle views A'-C' with circularly polarized light.

In the present embodiment, the lengths $l_M$, $l_{L1}$ and $l_{R1}$ are 1,234 mm for the beam path $S_M$ and 1,250 mm for each of the beam paths $S_{L1}$ and $S_{R1}$. Identically sized representations of the bottle views A', B' and C' in the image 7 are accomplished in this way. The lengths $l_M$, $l_{L1}$ and $l_{R1}$ result from the lengths of the beam paths $S_M$, $S_{L1}$ and $S_{R1}$ between the symmetry axis 41 of the bottle 3 and the image recording device 6, i.e. the front main plane of the objective lens.

Depending on the course of the beam paths $S_M$, $S_{L1}$ and $S_{R1}$ in the mirror cabinet 5 and the respective distances between the associated bottle views A'- C' in image 7, the absolute values of the lengths $l_M$, $l_{L1}$ and $l_{R1}$ as well as the ratio of said lengths may deviate from the embodiment. In practice, the values for $l_M$, $l_{L1}$ and $l_{R1}$ will be modified in the ray tracing operation until a simulated image 7 provides an optimum result.

However, when two identically sized bottle views A'-C', which are imaged side by side, are viewed, the longer beam path will always be the beam path having associated therewith in image 7 the bottle view that is imaged at a larger horizontal distance from the middle 8 of the image. In order to make this clear, two additional lateral image areas $L_2$ and $R_2$ with bottle views D' and E' are indicated by broken lines in FIG. 3. For producing them, additional beam paths $S_{L2}$ and $S_{R2}$ (not shown in FIGS. 1 and 2) would be necessary. It follows that, if the bottle views A' and C' are imaged in identical size, the beam path $S_{R1}$ will be longer than the beam path $S_M$, and if the bottle views B' and D' are imaged in identical size, the beam path $S_{L2}$ will have to be longer than the beam path $S_{L1}$.

The length ratio v of beam paths, which belong to bottle views positioned side by side in image 7, e.g. $l_{R1}/l_M$ or $l_{R2}/l_{R1}$, lies between 1.005 and 1.02. The demanded image definition is maintained within this range. The objective lenses are designed such that the lateral images are defined sharply especially in the case of longer distances.

The assignment of the bottle views A'-C' to the image areas M, $L_1$ and $R_1$ results from the optimization of the beam paths $S_M$, $S_{L1}$ and $S_{R1}$ provided in the mirror cabinet 5, This also applies to cases where the image 7 is divided into a number of image areas deviating from the above-mentioned one. The views A'-C' or other views may be arranged at angular distances deviating from those according to the present embodiment, e.g. at a distance of 15° or 45°.

The tilting angle $\alpha$ of the fixed mirror 11 is 0.45° in the present embodiment, the angle $\delta$ of the fixed mirror 14 is 0.2°. Depending on the respective position of the mirrors 11 and 14 in the beam paths $S_{L1}$ and $S_{R1}$, the values may deviate from the aforementioned ones. Suitable tilting angles $\alpha$ and $\gamma$ range from −1° to −0.01° and from 0.01° to 1°, the mirror surface being inclined at an oblique angle upwards in the case of positive values and at an oblique angle downwards in the case of negative values. The angles $\beta$ and $\delta$ are adjusted by means of the holders 19 and 20 such that the bottle views A'-C' are oriented vertically relative to one another and, in so doing, the distorted lines in the lateral image areas $L_1$ and $R_1$ are automatically compensated for. Also the absolute values of the adjusted angles $\beta$ and $\delta$ range from 0.01° to 1°, depending on the beam paths $S_{L1}$ and $S_{R1}$ optimized in the ray tracing process and depending on the position of the mirrors 11-14. In the beam paths $S_{L1}$ and $S_{R1}$ of the present embodiment, one mirror surface is inclined at an oblique angle upwards (mirrors 11 and 14) and another one is inclined at an oblique angle downwards (mirrors 12 and 13).

The sequence of the fixed and adjustable mirrors 11-14 in the beam paths $S_{L1}$ and $S_{R1}$, respectively, is irrelevant as regards the function of the mirror cabinet 5. It can be determined according to practical points of view, e.g. in accordance with space requirements or accessibility for the purpose of adjustment.

Making use of the common mirror 15, the demanded lengths $l_M$, $l_{L1}$ and $l_{R1}$ of the beam paths $S_M$, $S_{L1}$ and $S_{R1}$ can be realized in a space-saving array. The elevation of the image recording device 6 may deviate from that shown in the present embodiment. Likewise, the deflection mirror 15 is not absolutely necessary for the function of the mirror cabinet 5. The mirrors 9-15 may e.g. be conventional front surface mirrors.

The fixed mirror holders 16, 17 for the mirrors 9 and 10 as well as the holders and mounting bases for the other optical components can e.g. be cut from metal or they may consist of commercially available optical mounting elements, so that stable, orthogonal mounting on the base plate 23 will be guaranteed.

The fixed holders 18 and 21 are preferably cut from a metal, such as aluminium, and have a mounting surface for the mirrors 11 and 14, which is inclined according to the angles $\alpha$ and $\delta$ so that the tilting angles $\alpha$ and $\delta$ of said mirrors will be guaranteed without any additional adjustment of the elevation of said mirrors 11 and 14.

The holders 19 and 20 consist e.g. of a commercially available three-point adjustment unit including a base (not shown) so that the respective beam path can be tilted about a vertical axis, e.g. for compensating manufacturing and/or mounting tolerances, as well as about a horizontal axis for adjusting the elevation of the mirrors 12 and 13 and the angles $\beta$ and $\gamma$, respectively. By adequately positioning the mirrors of the mirror cabinet 5 and by a suitable selection of the elevation of individual mirrors, the generation of disturbing light reflections on the bottles can be minimized to a large extent or, ideally, avoided completely.

The base plate 23 is not limited to a specific material or a specific shape. The base plate 23 is preferably shaped such that it can be secured in position, together with the mirror cabinet 5 that has already been mounted, in a suitable mounting frame and/or housing (not shown). However, the base plate 23 comprises in any case a structure with one, or with a plurality of parallel mounting surfaces to which the optical components can be fixed, e.g. in mounting holes, in a stable manner and with the demanded tolerances.

The shield 31 is arranged between the mirror cabinet 5 and the light source 4 and prevents undesirable residual light reflections, as far as the latter have not already been minimized by a skilful arrangement of the mirrors, so as not to impair image evaluation. The shade 33 is arranged in the mirror cabinet 5 between the boundary rays of the imaging beam paths $S_M$, $S_{L1}$ and $S_{R1}$.

The mounting and the adjustment of the inspection apparatus 1 according to the present disclosure can be executed as follows:

the mirror cabinet 5 is mounted on the base plate 23 and the latter is secured in position in the inspection apparatus 1, e.g. in a mounting frame and/or a housing (not shown) Between the light source 4 and the mirror cabinet 5, a bottle 3 is established at an examination position and the bottle views A'-C' are imaged on the image areas M, L and R by means of the image recording device 6. By rotating and tilting the image recording device 6 in its holder (not shown), the bottle view A' imaged in area M is oriented orthogonally to a desired reference position in image 7.

By vertically tilting the mirror 12, the bottle view B' is brought into vertical (identical heights of the bottles in the image) alignment with view A' so that the two views A' and B' seem to be placed e.g. on the auxiliary line 27 indicated in FIG. 3. When a correct vertical alignment of the bottle view B' in image 7 has been accomplished, the elevation of the fixed mirror 11, i.e. the tilting angle α, will cooperate with the adjusted elevation of the adjustable mirror 12, i.e. the tilting angle β, in such a way that an image distortion caused by central projection will simultaneously be compensated for on the image area. This will avoid or reduce an image distortion in the case of which the upper area of the bottle view B' seems to be distorted towards the centre 8 of the image.

By horizontally tilting the adjustable mirror 12, production- and mounting-dependent tolerances will be compensated for in the beam path $S_{L1}$ and the bottle view B' will be adjusted to a desired horizontal position in the image area $L_1$. The above-mentioned adjustment steps can be executed in an arbitrary sequence.

The bottle view C' is aligned in the image area $R_1$ in an analogous manner by tilting the mirror 13. Simultaneously, the tilting angles γ and δ compensate, in common, the image distortion caused by central projection.

When the inspection apparatus 1 according to the present disclosure is used, the step-by-step adjustment of several mirrors of a beam path required in the case of conventional inspection apparatuses can be dispensed with, and the quality of the image will be improved at the same time. Due to the fixed elevation of the mirrors 11 and 14, reproducible conditions are provided for more efficient mounting. The size adaptation and the elimination of image distortion facilitate a correct evaluation of the bottle views A', B' and C'.

I claim:

1. An inspection apparatus for optically examining bottles, comprising:
   an image recording device for producing an image with a plurality of horizontally juxtaposed image areas, at least two of the image areas being arranged laterally of the middle of the image;
   a mirror cabinet comprising a plurality of beam paths for viewing a bottle to be examined in perspective at an oblique angle upwards and for deflecting, in the direction of the image areas different circumferential side views of the bottle, each beam path having provided therein separate deflection mirrors whose respective elevation is defined with respect to a base plate and,
   two of the separate deflection mirrors for beam paths associated with the lateral image areas are tilted relative to a normal to the base plate in such a way that an image distortion caused by central projection will be compensated for in the lateral image areas.

2. An inspection apparatus according to claim 1, wherein in the beam paths associated with the lateral image areas, the elevation of one of the separate deflection mirrors is fixed and the elevation of the other separate deflection mirror is adjustable.

3. An inspection apparatus according to claim 1, wherein in the beam paths associated with the lateral image areas, one separate deflection mirror is inclined at an oblique angle upwards and another separate deflection mirror is inclined at an oblique angle downwards.

4. An inspection apparatus according to claim 1, wherein in the beam paths associated with the lateral image areas, the absolute values of the tilting angles of the separate deflection mirrors relative to the normal to the base plate range from 0.01° to 1°.

5. An inspection apparatus according to claim 1, wherein the separate deflection mirrors for beam paths associated with the lateral image areas are tilted in such a way that the projected side views in the image are additionally oriented vertically to one another.

6. An inspection apparatus according to claim 1, wherein the separate deflection mirrors are, with a fixed elevation, secured in position on holders having a mounting surface that is inclined in accordance with the elevation of these deflection mirrors.

7. An inspection apparatus according to claim 1, wherein the separate deflection mirrors for the beam path associated with the central image area are arranged at right angles to the base plate.

8. An inspection apparatus according to claim 1, wherein each beam path has provided therein two separate deflection mirrors.

9. An inspection apparatus according to claim 1, wherein the base plate is oriented substantially at right angles to the symmetry axis of the bottle.

10. An inspection apparatus according to claim 1, wherein the beam paths associated with the lateral image areas are longer than the beam path associated with the central image area, the lengths of the beam paths being graded such that the side views of the bottle in the image areas have substantially the same size.

11. An inspection apparatus according to claim 1, wherein the length of the beam paths associated with the lateral image areas increases as the distance between the image area associated with the respective beam path and the middle of the image increases, the lengths of the beam paths being graded such that the side views of the bottle in the image areas have substantially the same size.

12. An inspection apparatus according to claim 10, wherein the length ratio of beam paths associated with juxtaposed image areas lies between 1.005 and 1.02.

13. An inspection apparatus according to claim 1, wherein the inspection apparatus additionally comprises a light source for exposing the bottle to one of incident light, transmitted light, or a combination thereof.

14. An inspection apparatus according to claim 13, wherein a shade is provided between the beam paths, the shade preventing light reflections in bottle images that would disturb an evaluation of said images.

* * * * *